United States Patent [19]
Mori et al.

[11] Patent Number: 5,426,238
[45] Date of Patent: Jun. 20, 1995

[54] METHOD FOR PRODUCING AN ALDEHYDE

[75] Inventors: Tomoyuki Mori; Akio Ueda; Kouichi Fujita, all of Kurashiki, Japan

[73] Assignee: Mitsubishi Kasei Corporation, Tokyo, Japan

[21] Appl. No.: 249,848

[22] Filed: May 26, 1994

[30] Foreign Application Priority Data

Jun. 10, 1993 [JP] Japan .................. 5-138630

[51] Int. Cl.⁶ ............................ C07C 45/50
[52] U.S. Cl. ...................... 568/454; 568/452; 568/453
[58] Field of Search ............ 568/454, 492, 453, 452

[56] References Cited

U.S. PATENT DOCUMENTS

| | | | |
|---|---|---|---|
| 4,523,036 | 6/1985 | Cornils et al. | 568/454 |
| 4,567,305 | 1/1986 | Matsumoto et al. | 568/454 |
| 4,577,043 | 3/1986 | Kalbfell et al. | 568/454 |
| 4,827,043 | 5/1989 | Butler | 568/492 |
| 5,105,018 | 4/1992 | Miyazawa et al. | 568/453 |

OTHER PUBLICATIONS

J. Chem. Soc. (A), (4) 1968, D. Evans et al., "The Reaction of Hydridocarbonyltris (Triphenylphosphine)Rhodium with Carbon Monoxide, and of the Reaction Products, Hydridodicarbonylbis(Triphenylphosphine)Rhodium and Dimeric Species, with Hydrogen ", pp. 2660–2665.

Indications The International Journal of Davy McKee, (6) 1982/1983, J. L. Stewart, "LP Oxo Process—A Success Story", pp. 20–28.

Primary Examiner—Werren B. Lone
Attorney, Agent, or Firm—Oblon, Spivak, McClelland, Maier & Neustadt

[57] ABSTRACT

A method for producing an aldehyde, which comprises reacting an olefin with carbon monoxide and hydrogen in a hydroformylation reaction zone in the presence of a rhodium catalyst having an organophosphorus compound as a ligand, wherein a reaction solution withdrawn from the hydroformylation reaction zone, which contains an unreacted olefin, an aldehyde product and the catalyst, is countercurrently contacted with carbon monoxide and hydrogen in a contact tower to separate and recover the unreacted olefin without substantially deactivating the rhodium catalyst and supplying the recovered unreacted olefin together with the carbon monoxide and the hydrogen to the hydroformylation reaction zone.

15 Claims, 1 Drawing Sheet

METHOD FOR PRODUCING AN ALDEHYDE

BACKGROUND OF THE INVENTION

1. Field of the Invention

The present invention relates to an improved method for hydroformylation which comprises reacting an olefin with carbon monoxide and hydrogen in a hydroformylation reaction zone in the presence of a rhodium catalyst having an organophosphorus compound as a ligand. More particularly, the present invention relates to a method for hydroformylation of an olefin, which is characterized in that an unreacted olefin is recovered efficiently and economically from a reaction solution withdrawn from the hydroformylation reaction zone without substantially deactivating the rhodium catalyst, and the recovered unreacted olefin is supplied to the hydroformylation reaction zone.

2. Discussion of Background

A method has heretofore been known wherein the hydroformylation reaction of an olefin is carried out in the presence of a rhodium catalyst. Further, several methods have been disclosed for separating an unreacted olefin, an aldehyde product and the catalyst from the reaction solution of hydroformylation.

For example, in Japanese Unexamined Patent Publication No. 125103/1977, an unreacted olefin, hydrogen, carbon monoxide and an aldehyde product are stripped by a gas stripping reaction system by means of a single step complete mixing tank, and their vapor mixture is cooled and then subjected to flash separation to separate the aldehyde product from the unreacted olefin, hydrogen and carbon monoxide. It is disclosed that the major proportion of the gas stream containing the separated unreacted olefin is recycled to the reaction zone.

However, in such a case, it is apparently impossible to completely separate the olefin only by the flash separation, since the olefin has a large latent heat for distillation, and there will be a substantial loss of the olefin.

To prevent such a substantial loss of an olefin, Japanese Unexamined Patent Publication No. 101633/1991 discloses a method for recovering an olefin by means of a scrubber installation. In such a recovery method, however, the olefin and aldehydes are absorbed by a stripped catalyst solution and recycled to the reaction apparatus, whereby high boiling point products such as dimmers and trimmers formed by self condensation of aldehydes or esters are expected to increase.

Further, Japanese Unexamined Patent Publication No. 70634/1984 discloses a method for producing an aldehyde which comprises reacting an olefin with carbon monoxide and hydrogen in the presence of a water-soluble rhodium-phosphine complex compound, wherein as a method for recovering an unreacted olefin, a stripping tower by means of a synthetic gas, is employed. However, in this method, the catalyst solution is separated into a water tank in the water phase-organic phase separation step prior to introduction to the stripping tower, and therefore the catalyst solution is not substantially contained.

Still further, Japanese PCT Publication No. 502449/1991 discloses a method of intimately contacting at least a part of the stream of the hydroformylation reaction product with carbon monoxide and a hydrogen-supplying substance. However, in this method, the stream of the reaction product is withdrawn as a steam stream from the upper portion of the reactor, and therefore the catalyst is not contained in the stream of the reaction product.

On the other hand, J. Chem. Soc. (A), 1968, p. 2660 et seq, discloses that a dimmer will be formed by contacting carbon monoxide and hydrogen to Rh hydride complex under atmospheric pressure at room temperature, whereby deterioration of the activity of the Rh catalyst is expected.

Thus, a method for recovering an unreacted olefin without reducing the catalytic activity from a reaction production stream containing a catalyst solution as in a liquid-circulation process as described e.g. in U.S. Pat. No. 4,148,830, has not been known.

By conventional techniques, it has been difficult to recover an unreacted olefin by means of a countercurrent contact tower when the hydroformylation reaction is carried out in the presence of a Rh catalyst in a liquid-circulating process wherein a reaction solution withdrawn from the reaction zone contains a catalyst solution, since deterioration of the activity of the Rh catalyst will result.

SUMMARY OF THE INVENTION

It is an object of the present invention to provide a method for recovering an unreacted olefin economically and efficiently without substantially deactivating the catalyst in a countercurrent contact tower in such a liquid-circulating process.

The present inventors have conducted extensive studies on the above problems and as a result, have found it possible to solve such problems by countercurrently contacting the reaction solution withdrawn from the hydroformylation reaction zone with carbon monoxide and hydrogen to be introduced in the hydroformylation reaction zone, intimately under a specific operational condition. The present invention has been accomplished on the basis of this discovery.

Thus, the present invention provides a method for producing an aldehyde, which comprises reacting an olefin with carbon monoxide and hydrogen in a hydroformylation reaction zone in the presence of a rhodium catalyst having an organophosphorus compound as a ligand, wherein a reaction solution withdrawn from the hydroformylation reaction zone, which contains an unreacted olefin, an aldehyde product and the catalyst, is countercurrently contacted with carbon monoxide and hydrogen in a contact tower to separate and recover the unreacted olefin without substantially deactivating the rhodium catalyst and supplying the recovered unreacted olefin together with the carbon monoxide and the hydrogen to the hydroformylation reaction zone.

DETAILED DESCRIPTION OF THE PREFERRED EMBODIMENTS

Figure 1:
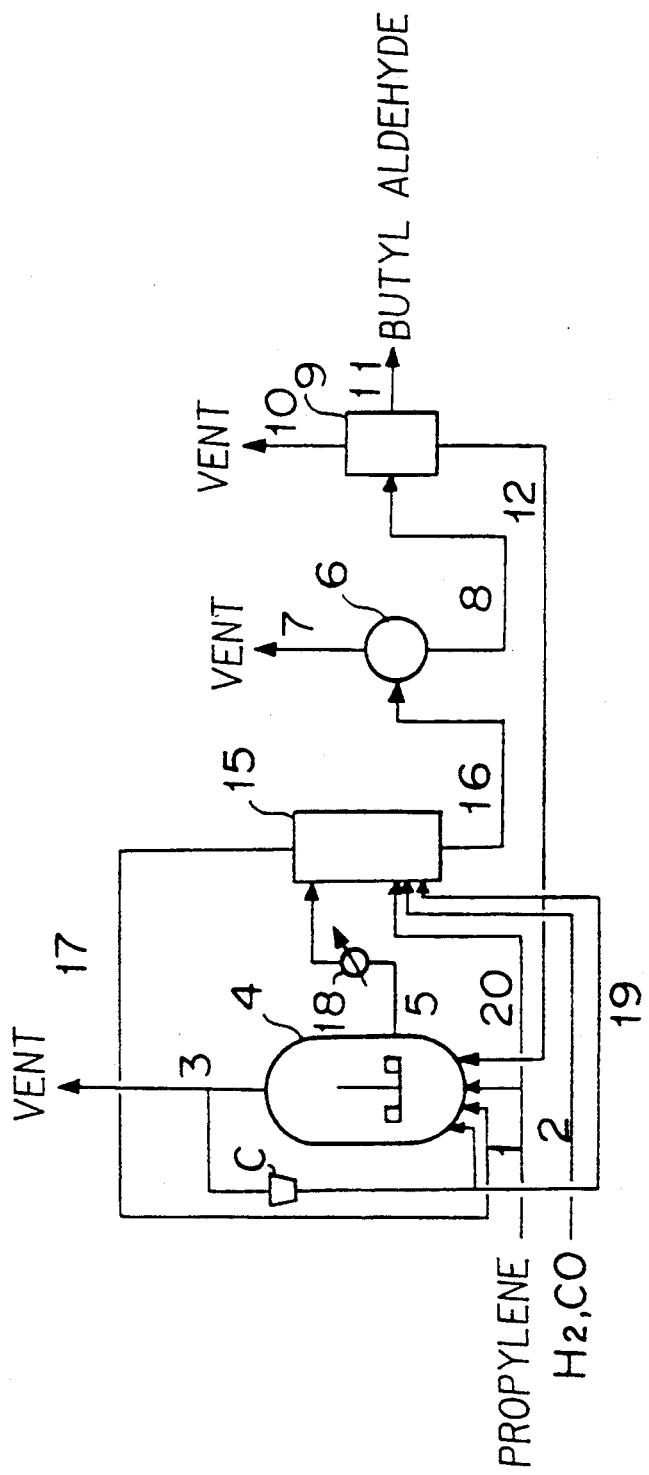
FIG. 1 shows a flow diagram for Examples and Comparative Examples, wherein reference numeral 4 indicates an agitation tank type reactor, numeral 6 a gas-liquid separator, numeral 9 an aldehyde-separating tower, numeral 15 a countercurrent contact tower, numeral 18 a heat exchanger, and C a compressor.

Now, the present invention will be described in detail.

With respect to the olefin to be used in the present invention, there is no critical limitation, and a single olefin or an olefin mixture may be employed. However, preferred olefins are olefins having from 2 to 5 carbon atoms or their mixtures. The most preferred olefin is propylene. Further, a starting material having low olefin purity such as the one containing hydrocarbons other than olefin, such as paraffins, may also be suitably employed.

The starting material olefin may be used usually without any special pretreatment. However, it is possible to employ the one having a sulfur content or halogen content known as a catalyst poison, or dienes and trienes, or peroxides, removed by conventional methods such as adsorption, extraction, distillation, heat treatment or separation by means of membranes.

As the catalyst, a rhodium catalyst having an organophosphorus compound as a ligand is employed. The organic phosphorus compound may, for example, be a trialkylphosphine such as tributylphosphine or trioctylphosphine, a triarylphosphine such as triphenylphosphine, tritolylphosphine, or a triarylphosphine having hydrogen of a phenyl group substituted by a sulfonic group or halogen, a tricycloalkylphosphine such as tricyclohexylphosphine, an alkylarylphosphine such as monobutyldiphenylphosphine or dipropylphenylphosphine, a cycloalkylarylphosphine, or an alkylcycloalkylphosphine. Further, a trialkyl phosphite, a triaryl phosphite such as triphenyl phosphite or trinaphthyl phosphite which may have a substituent, or an alkylaryl phosphite may also be employed. Specifically, compounds disclosed in U.S. Pat. Nos. 3,415,906, 4,599,206, 4,351,759, 4,748,261, 4,567,306, 5,235,113 and 5,227,532 may be mentioned. However, the present invention is by no means restricted by the type of the organophosphorus compound.

Two or more members among these organophosphorus compounds may be employed as mixed ligands. Further, the above organophosphorus compound may be used in combination with a pentavalent organophosphorus compound such as triphenylphosphine oxide.

As the rhodium source, an organic salt such as rhodium acetyl acetonate or rhodium acetate, an inorganic salt such as rhodium nitrate or an oxide such as rhodium oxide may also be used other than a rhodium complex such as hydride carbonyltris(triphenylphosphine)rhodium or acetoxy bis(triphenylphosphine)rhodium. Rhodium may directly be supplied to the hydroformylation reactor. However, it is also possible that rhodium is treated together with a ligand of an organophosphorus compound with carbon monoxide and hydrogen under an elevated temperature and pressure in a solvent outside the reactor to preliminarily prepare a catalyst solution. The solvent for the preparation of this catalyst is usually selected from the solvents for reaction which will be described hereinafter. However, such a solvent may not necessarily be the same as the solvent for reaction. With respect to the conditions for preparation of the catalyst, the rhodium concentration is usually from a few ppm to a few wt %, the molar ratio of the ligand of the organophosphorus compound to rhodium is usually P/Rh=1 to 10,000, the temperature is from 60° to 200° C., the pressure is from atmospheric pressure to 200 kg/cm²G, and the treating time is within a range of from a few minutes to some dozen hours.

The above treatment may be carried out in a batch system or a continuous system.

As the solvent for the hydroformylation reaction, the olefin itself may be used, or the resulting aldehyde or high boiling point substances produced as by-products may be used as the solvent. Further, a solvent which is capable of dissolving the catalyst and which presents no adverse effects to the reaction, for example, an aliphatic hydrocarbon such as hexane or octane, an aromatic hydrocarbon such as toluene or xylene, an alicyclic hydrocarbon such as cyclohexane, an alcohol such as butanol, octanol, polyethylene glycol or polypropylene glycol, an ether such as trigrime or tetragrime, an ester such as dioctyl phthalate, or water, may also be used. With respect to the hydroformylation reaction conditions, the hydrogen partial pressure is usually from 0.1 to 200 kg/cm²G, the carbon monoxide partial pressure is from 0.1 to 200 kg/cm²G, the total pressure is from a few kg/cm²G to 300 kg/cm²G, the ratio of hydrogen partial pressure/carbon monoxide partial pressure=0.1 to 10, the temperature is from 60° to 200° C., the rhodium concentration is from a few wt ppm to a few wt %, P (in the organophosphorus compound ligand)/Rh=1 to 10,000 (molar ratio), and the reaction time is from a few minutes to some dozen hours.

The reaction solution thus withdrawn is introduced to an upper portion of a countercurrent contact tower having a theoretical plate number of from 4 to 100 plates without pressure release i.e. substantially under the same pressure as in the reaction zone. If the theoretical plate number of the countercurrent contact tower is less than 4 plates, the aldehyde product will accompany the unreacted olefin, such being undesirable. Further, if the theoretical plate number is more than 100 plates, such brings about an unnecessary increase of the installation costs.

On the other hand, carbon monoxide and hydrogen are introduced to the tower bottom and countercurrently contacted to the above reaction solution withdrawn from the reaction zone, whereupon the unreacted olefin obtained from the tower top will be recycled together with the carbon monoxide and hydrogen to the hydroformylation reaction zone. In such a case, the operational conditions of the countercurrent contact tower are maintained so that the residence time in the countercurrent contact tower is within 4 hours, preferably from 0.01 to 4 hours, and the tower bottom temperature is within a range of from 50° to 150° C., and the residence time and the tower bottom temperature are mutually adjusted so that value F will be at most 0.35, preferably from 0.01 to 0.35, when the following equation is employed in calculating the value F:

$$F = \theta * \exp[10,000((1/383) - (1/(T+273)))]$$

where $\theta$ is the residence time (hrs) and T is the tower bottom temperature (°C.) whereby the unreacted olefin can be separated and recovered from the reaction solution without substantially deactivating the rhodium catalyst (the method as defined in Claim 2). If the tower bottom temperature of the countercurrent contact tower is lower than 50° C., the recovery rate of the unreacted olefin tends to be low. On the other hand, if it exceeds 150° C., by-products tend to increase, and the catalytic activity of the rhodium catalyst tends to deteriorate, such being undesirable.

In the present invention, the residence time $\theta$ represents the tower bottom residence time of the liquid discharged from the contact tower bottom.

Further, if a condition where value F calculated by the above equation exceeds 0.35, is employed, the deactivation of the rhodium catalyst will be substantial, such being disadvantageous from the viewpoint of practical industrial application.

As another method for preventing deactivation of the rhodium catalyst, the olefin may be permitted to be present at the bottom of the countercurrent contact tower so that the molar ratio of the olefin/Rh is at least 0.6, preferably within a range of from 1.0 to 50, whereby the object of the present invention can be attained (the method as defined in Claim 3). When a condition where the molar ratio of the olefin/Rh is less than 0.6, is employed, deterioration of the catalytic activity of the rhodium catalyst tends to result. On the other hand, if the molar ratio is too high, the olefin will be supplied excessively.

As a manner in which the olefin is permitted to be present at the bottom of the countercurrent contact tower, a method may be employed wherein the olefin or a gas or liquid stream containing the olefin is partially supplied to the tower bottom, or a method may be employed wherein a countercurrent contact tower having a theoretical plate number smaller than the theoretical plate number required for completely recovering the unreacted olefin from the top of the contact tower, is employed.

The method of the present invention can be carried out by a combination of the methods defined in Claims 2 and 3. However, the object of the present invention i.e. to recover the unreacted olefin without substantially deactivating the rhodium catalyst, can adequately be accomplished by employing either one of the methods.

In the present invention, "without substantially deactivating the rhodium catalyst" means that the deactivating rate of the rhodium catalyst is not more than 1%/day.

The catalyst solution containing the aldehyde product, which is discharged from the tower bottom of the countercurrent contact tower is subjected to a conventional method such as distillation in a subsequent step to separate the aldehyde product, and the solution containing the solvent and the catalyst can be recycled to the hydroformylation reaction zone.

Now, specific embodiments of the present invention will be described in further detail with reference to Examples. However, it should be understood that the present invention is by no means restricted by such specific Examples.

EXAMPLES 1 TO 8 AND COMPARATIVE EXAMPLES 1 TO 3

Using an apparatus as shown in FIG. 1, a hydroformylation reaction of propylene was carried out. With respect to the conditions of the catalyst solution in a pipeline (12), Rh was 330 mg/l, and triphenylphosphine (hereinafter referred to simply as TPP) was 21.1 wt %. The reactor (4) was maintained at 100° C. under a total pressure of 17 kg/cm$^2$G, propylene (pipeline 1) was charged at a rate of 7.5 kg/Hr, whereupon butylaldehyde (pipeline 11) was formed at a rate of 11.8 kg/hr. The propylene (pipeline 1) used had a purity of 99 mol %, and water gas (pipeline 2) used was a gas with $H_2+CO=98.8\%$ and a $H_2/CO$ ratio of 1.015. They were supplied to maintain the pressure of the reactor (4) at a level of 17 kg/cm$^2$G. Inert gas and a part of unreacted material were discharged from a vent (3). The reaction solution withdrawn from the reactor (4) was supplied through a pipeline (5) to the top of a countercurrent contact tower (15). A heat exchanger (18) was used for heating or cooling to adjust the feed temperature to the countercurrent contact tower. An unreacted olefin obtained from the top of the countercurrent contact tower (15) was recycled through a pipeline (17) together with carbon monoxide and hydrogen to the reactor (4). Further, the formed aldehyde was withdrawn from the bottom of the countercurrent contact tower (15) and supplied through a pipeline (16) to a gas liquid separator (6) and then through a pipeline (8) to an aldehyde-separating tower (9). Waste gases from the gas-liquid separator (6) and the tower (9) are discharged from vents (7) and (10), respectively. Further, a pipeline (20) was provided to supply propylene to the tower bottom of the countercurrent contact tower (15), and a pipeline (19) was provided to supply a part of a recycle gas containing propylene.

The countercurrent contact tower was operated by changing the operational conditions of the contact tower as identified in Tables 1 and 2, whereby the deactivation rate of the catalyst rhodium was as shown in Tables 1 and 2.

TABLE 1

| | Examples | | | | | | | |
|---|---|---|---|---|---|---|---|---|
| | 1 | 2 | 3 | 4 | 5 | 6 | 7 | 8 |
| Counter-current contact tower | | | | | | | | |
| Theoretical plate number (plates) | 100 | 100 | 12 | 12 | 12 | 12 | 4 | 12 |
| Feed temp. (°C.) | 100 | 100 | 165 | 165 | 165 | 165 | 155 | 165 |
| Tower top temp. (°C.) | 89 | 89 | 151 | 147 | 147 | 149 | 140 | 147 |
| Tower bottom temp. (°C.) | 71 | 71 | 108 | 110 | 110 | 110 | 111 | 110 |
| PPY concentration at the bottom (ppm) | 0 | 0 | 2060 | 115 | 118 | 968 | 864 | 118 |
| PPY/Rh mol ratio at the bottom | 0 | 0 | 19.3 | 1.1 | 1.1 | 9.0 | 8.1 | 1.1 |
| PPY charge (kg/hr) at the bottom (pipeline 20) | 0 | 0 | 0 | 0.013 | 0 | 0 | 0 | 0 |
| Recycle gas (pipeline 19) | | | | | | | | |
| Gas flow rate (mol/hr) | 0 | 0 | 94.6 | 0 | 1.1 | 11.2 | 0 | 1.1 |
| PPY concentration (mol %) | — | — | 13 | — | 27 | 23 | — | 27 |
| Residence time (hr) at the bottom | 0.4 | 4.0 | 0.4 | 0.4 | 0.4 | 0.4 | 0.4 | 2.0 |
| Value F | 0.02 | 0.2 | 0.35 | 0.4 | 0.4 | 0.4 | 0.43 | 2.0 |
| Deactivating rate[1] of Rh catalyst (%/day) | 1> | 1> | 1> | 1> | 1> | 1> | 1> | 1> |

[1] Calculated from the amount of formed aldehydes (mol/g · catalyst · hr)

TABLE 2

| | Comparative Examples | | |
|---|---|---|---|
| | 1 | 2 | 3 |
| Counter-current contact tower | | | |

TABLE 2-continued

| | Comparative Examples | | |
|---|---|---|---|
| | 1 | 2 | 3 |
| Theoretical plate number (plates) | 12 | 100 | 100 |
| Feed temp. (°C.) | 165 | 150 | 220 |
| Tower top temp. (°C.) | 147 | 127 | 212 |
| Tower bottom temp. (°C.) | 110 | 100 | 150 |
| PPY concentration at the bottom (ppm) | 0 | 0 | 0 |
| PPY/Rh mol ratio at the bottom | 0 | 0 | 0 |
| PPY charge (kg/hr) at the bottom (pipeline 20) | 0 | 0 | 0 |
| Recycle gas (pipeline 19) | | | |
| Gas flow rate (mol/hr) | 0 | 0 | 0 |
| PPY concentration (mol %) | — | — | — |
| Residence time (hr) at the bottom | 0.4 | 2.0 | 0.4 |
| Value F | 0.4 | 1.0 | 4.7 |
| Deactivating rate[1] of Rh catalyst (%/day) | 15 | 5 | Deactivated |

[1]Calculated from the amount of formed aldehydes (mol/g · catalyst · hr)

According to the method of the present invention, the unreacted olefin can be separated and recovered from the reaction solution containing the rhodium catalyst without substantially deactivating the catalyst and can be recycled to the reaction zone economically and efficiently. Thus, the method of the present invention is highly advantageous in an industrial application.

What is claimed is:

1. A method for producing an aldehyde, which comprises reacting an olefin with carbon monoxide and hydrogen in a hydroformylation reaction zone in the presence of a rhodium catalyst having an organophosphorus compound as a ligand, wherein a reaction solution withdrawn from the hydroformylation reaction zone, which contains an unreacted olefin, an aldehyde product and the catalyst, is countercurrently contacted with carbon monoxide and hydrogen in a contact tower to separate and recover the unreacted olefin without substantially deactivating the rhodium catalyst and supplying the recovered unreacted olefin together with the carbon monoxide and the hydrogen to the hydroformylation reaction zone.

2. The method for producing an aldehyde according to claim 1, wherein the countercurrent contact is carried out by maintaining the residence time in the contact tower within 4 hours and the tower bottom temperature within a range of from 50° to 150° C. and mutually adjusting the residence time and the tower bottom temperature so that value F will be at most 0.35 when the following equation is employed in calculating the value F:

$$F=\theta^{*}\exp[10{,}000((1/383)-(1/(T+273)))]$$

where $\theta$ is the residence time (hrs) and T is the tower bottom temperature (°C.).

3. The method for producing an aldehyde according to claim 1, wherein the countercurrent contact is carried out in the presence of the olefin at the tower bottom of the contact tower so that the olefin/Rh molar ratio will be at least 0.6.

4. The method for producing an aldehyde according to claim 3, wherein the countercurrent contact is carried out in the presence of the olefin at the tower bottom of the contact tower so that the olefin/Rh molar ratio will be within a range of from 1.0 to 50.

5. The method for producing an aldehyde according to claim 3, wherein the olefin is permitted to be present at the tower bottom of the contact tower in such a manner that the olefin or a gas or liquid stream containing the olefin is partially supplied to the tower bottom.

6. The method for producing an aldehyde according to claim 1, wherein the olefin is ethylene, and the aldehyde product is propanal.

7. The method for producing an aldehyde according to claim 1, wherein the olefin is propylene, and the aldehyde product is n-butanal and isobutanal.

8. The method for producing an aldehyde according to claim 5, wherein the olefin is propylene, and the aldehyde product is n-butanal and isobutanal.

9. The method for producing an aldehyde according to claim 1, wherein the olefin is butene, and the aldehyde product is a mixture of linear pentanal and branched pentanals.

10. A method for producing an aldehyde, which comprises reacting an olefin with carbon monoxide and hydrogen in a hydroformylation reaction zone in the presence of a rhodium catalyst having an organophosphorus compound as a ligand, wherein a reaction solution withdrawn from the hydroformylation reaction zone, which contains an unreacted olefin, an aldehyde product and the catalyst, is countercurrently contacted with carbon monoxide and hydrogen in a contact tower to separate and recover the unreacted olefin under the condition that the countercurrent contact is carried out by maintaining the residence time in the contact tower within 4 hours and the tower bottom temperature within a range of from 50° to 150° C. and mutually adjusting the residence time and the tower bottom temperature so that the value F will be at most 0.35 when the following equation is employed in calculating the value F:

$$F=\theta^{*}\exp(10{,}000((1/383)-(1/(T+273))))$$

where $\theta$ is the residence time (hrs) and T is the tower bottom temperature (°C.), in the presence of the olefin at the tower bottom of the contact tower so that the olefin/Rh molar ratio will be at least 0.6, and supplying the recovered unreacted olefin together with the carbon monoxide and the hydrogen to the hydroformylation reaction zone.

11. The method for producing an aldehyde according to claim 10, wherein the countercurrent contact is carried out in the presence of the olefin at the tower bottom of the contact tower so that the olefin/Rh molar ratio will be within a range of from 1.0 to 50.

12. The method for producing an aldehyde according to claim 10, wherein the olefin is permitted to be present at the tower bottom of the contact tower in such a manner that the olefin or a gas or liquid stream containing the olefin is partially supplied to the tower bottom.

13. The method for producing an aldehyde according to claim 4, wherein the olefin is permitted to be present at the tower bottom of the contact tower in such a manner that the olefin or a gas or liquid stream containing the olefin is partially supplied to the tower bottom.

14. The method for producing an aldehyde according to claim 10, wherein the olefin is propylene, and the aldehyde product is n-butanal and isobutanal.

15. The method for producing an aldehyde according to claim 10, wherein the olefin is butene, and the aldehyde product is a mixture of linear pentanal and branched pentanals.

* * * * *